United States Patent [19]
Imamura et al.

[11] Patent Number: 4,650,862
[45] Date of Patent: Mar. 17, 1987

[54] SUGAR PHOSPHATES
[75] Inventors: Takashi Imamura; Shigeto Kayane, both of Wakayama; Tomihiro Kurosaki, Oosaka, all of Japan
[73] Assignee: Kao Corporation, Tokyo, Japan
[21] Appl. No.: 753,058
[22] Filed: Jul. 9, 1985
[30] Foreign Application Priority Data
Jul. 9, 1984 [JP] Japan .................................. 59-141780
[51] Int. Cl.$^4$ .............................................. C07H 11/04
[52] U.S. Cl. ................................... 536/17.1; 536/117; 536/18.7
[58] Field of Search ................................ 536/117, 17.1
[56] References Cited
U.S. PATENT DOCUMENTS 3,103,507  9/1963  Knoevenagel ...................... 536/117
3,355,436 11/1967  Lutz et al. .......................... 536/117
3,375,168  3/1968  Curtin et al. ........................ 536/117
3,530,205  9/1970  Patton, Jr. et al. ................. 536/17.1
4,481,196 11/1984  Teraji et al. ........................ 536/117

Primary Examiner—Johnnie R. Brown
Attorney, Agent, or Firm—Oblon, Fisher, Spivak, McClelland & Maier

[57] ABSTRACT

Sugar phosphate of the following general formula (I):

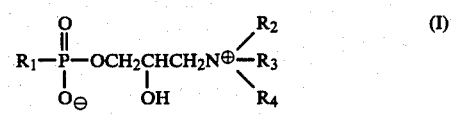

is prepared by reaction between a phosphoric monoester and a glycidyltriammonium salt.

The sugar phosphate according to the invention has good moisture retention and good adsorptivity on hair, and can be used in shampoos, rinses and cosmetics.

10 Claims, No Drawings

SUGAR PHOSPHATES

BACKGROUND OF THE INVENTION (i) Field of the Invention:

This invention relates to novel sugar phosphates and more particularly, to sugar phosphates of the following general formula (I)

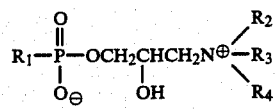

in which $R_1$ represents an active hydrogen residue of a hexose, and $R_2$, $R_3$ and $R_4$ are the same or different and represent a saturated or unsaturated hydrocarbon group having from 1 to 4 carbon atoms.

(ii) Description of the Prior Art:

In order to impart a soft feel to hair, it is the usual practice to add humectants to shampoos, rinses and hair cosmetics. Conventional humectants are, for example, propylene glycol, glycerine, urea, sorbitol, alkylene oxide adducts of alcohols, and the like. However, these substances are not satisfactory with respect to moisture retention and moisture absorption rate.

It is known that compounds having good moisture retention and moisture absorption have hydroxyl groups, polyether groups and the like and that compounds having N-cations exhibit high adsorptivity on hair. In order to satisfy the above requirements, there has been provided cationized cellulose in which N-cations are introduced into compounds having hydroxyl groups, such as sugars. However, such product has a disadvantage in that it is sticky and objectionable to the touch, and is not satisfactory as the humectant.

Accordingly, there is a demand for development of compounds which have good moisture retention and good adsorptivity on hair and which can be used by incorporation in shampoos, rinses and cosmetics.

SUMMARY OF THE INVENTION

Under these circumstances, we made intensive studies on such compounds and, as a result, found that sugar phosphates of the general formula (I) indicated before meet the demand. The present invention is accomplished on the basis of the above finding.

Accordingly, the present invention is to provide novel sugar phosphates of the general formula (I) which are useful as the humectant. The invention also provides a novel method for preparing such sugar phosphates.

DETAILED DESCRIPTION OF THE INVENTION AND PREFERRED EMBODIMENTS

The active hydrogen residue of a hexose represented by $R_1$ in the general formula (I) is intended to mean a hexose molecule from which one hydrogen atom in the hydroxyl group is eliminated. Example of the hexose include allose, altrose, galactose, glucose, gulose, idose, mannose, talose, fructose and the like. The other hydroxyl groups of these hexoses may be protected with protective groups. The protective groups include, for example, acetyl, benzyl, benzoyl, methyleneacetal, ethylideneacetal, benzylideneacetal, isopropylideneacetal, and the like. The saturated or unsaturated hydrocarbon groups having from 1 to 4 carbon atoms, represented $R_2$, $R_3$ and $R_4$, include, for example, methyl, ethyl, propyl, butyl, ethenyl, propenyl, butenyl, butadienyl, ethynyl, propynyl, butynyl, butadiynyl, and the like.

The sugar phosphates of the invention are prepared by reaction between phosphoric monoesters (II) and glycidyltrialkylammonium salts (III), for example, according to the following formula

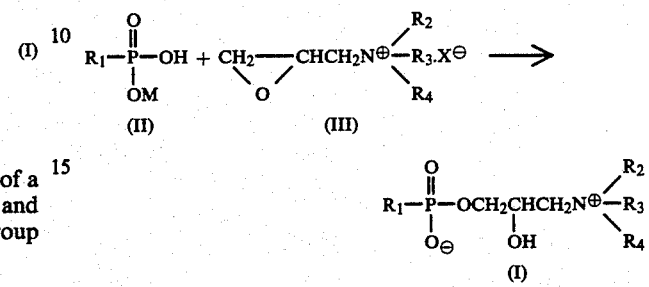

in which M represents an alkali metal, X represents an anion, and $R_1$, $R_2$, $R_3$ and $R_4$ have, respectively, the same meanings as defined before.

The phosphoric monoester of the formula (II) is a hexose phosphate-monoalkali metal salt and specific examples of the monoesters include monoalkali metal salts of glucose-1-phosphoric acid, glucose-6-phosphoric acid, mannose-1-phosphoric acid, mannose-6-phosphoric acid, galactose-1-phosphoric acid, galactose-6-phosphoric acid, fructose-1-phosphoric acid, fructose-6-phosphoric acid, and the like. The anions represented by X include, for example, chlorine, bromine, and the like.

In order to carry out the method of the invention, the glycidylalkylammonium salt (III) is used for reaction in an amount of 1 to 10 times by mole, preferably from 1 to 5 times by mole, to the phosphoric monoester of the formula (II). The reaction is conducted in an inert solvent at a temperature of from 30 to 150° C., preferably from 40 to 90° C. Examples of the inert solvent include polar solvents such as water, methanol, ethanol, isopropanol and the like. Of these, water is preferred.

The reaction product usually comprises, aside from the sugar ester of the general formula (I) of the invention, side products such as inorganic salts, unreacted phosphates, and glycidyltrialkylammonium salt or epoxy ring-opened substances thereof. The ratios of the respective components in the reaction product depend on the types of phosphoric monoester and glycidyltrialkylammonium salt, the molar ratio of the monoester and the salt, the type and amount of solvent, and the reaction conditions including reaction temperature.

Accordingly, the reaction product may be used, as it is, depending on the purpose in end use. However, if a product of a higher purity is needed, the reaction product can be purified by electrodialysis using an ion-exchange membrane, thereby obtaining sugar phosphate (I) having a purity as high as over 99%. More particularly, when ionic compounds are removed by an electrolytic technique using commercially sold ion-exchange membranes including, for example, cation exchange membranes such as C66-5T (made by Tokuyama Soda Co., Ltd.), CMV (made by Asahi Glass Co., Ltd.) and the like, and anion exchange membranes such as ACH-45T (made by Tokuyama Soda Co., Ltd.), AMV (made by Asahi Glass Co., Ltd.) and the like, the amphoteric sugar phosphate (I) alone remains amount the reaction products, i.e. the other impurities are removed. When water is distilled off from the residue, the sugar phosphate of high purity is obtained.

The thus obtained sugar phosphates (I) of the present invention have good moisture retention and can be used in shampoos, rinses and cosmetics.

The present invention is more particularly described by way of examples.

EXAMPLE 1

Alpha-D-glucopyranose,1-(2-hydroxy-3-N,N,N-trimethylammonium propylphosphate:

One hundred parts by weight of alpha-D-glucose-1-phosphate monosodium salt and 89.8 parts by weight of water were placed in a reactor and heated to 60° C. While keeping the reaction system at 60° C., a solution of 161 parts by weight of glycidyltrimethylammonium chloride in 143 parts by weight of water was gradually dropped into the system, followed by reaction at 60° C. for 4 hours. After completion of the reaction, floating impurities were removed by filtration. The solution was passed to an electrodialyser in which ionic impurities were desalted, followed by removing water from the reaction solution by distillation to obtain 108 parts by weight of a white powder. The thus obtained powder was analyzed and confirmed to be the intended compounds. The results of the analyses are shown below.

| Elemental Analysis (wt %): | C | N | H | P |
|---|---|---|---|---|
| calculated for $C_{12}H_{26}O_{10}NP$ | 38.4 | 3.7 | 6.9 | 8.3 |
| found | 38.2 | 3.7 | 6.6 | 8.0 |

Proton NMR (ppm), solvent: $D_2O$
$\delta 3.22$ (s,9H), 3.29–4.10 (m,12H), 5.40 (q,1H)
Other analyses:
Chlorine anion (wt %): 0.08
Total chlorine (wt %): 0.09
Water content (wt %): 1.32

EXAMPLE 2

Alpha-D-glucopyranose, 1-(2-hydroxy-3-N,N,N-trimethylammonium propylphosphate:

One hundred parts by weight of alpha-D-glucose-1-phosphate disodium salt (trihydrate) was placed in a reactor and dissolved in 69.8 parts by weight of an aqueous 4N hydrochloric acid solution and 72.9 parts by weight of water, followed by heating to 60° C. While keeping the reaction system at 60° C., a solution of 126 parts by weight of glycidyltrimethylammonium chloride in 184 parts by weight of water was gradually dropped into the reaction system, followed by reaction at 60° C. for 5 hours. After completion of the reaction, the reaction product was purified in the same manner as in Example 1, thereby obtaining 87 parts by weight of the intended compound.

| Elemental Analysis (wt %): | C | N | H | P |
|---|---|---|---|---|
| calculated for $C_{12}H_{26}O_{10}NP$ | 38.4 | 3.7 | 6.9 | 8.3 |
| found | 38.0 | 3.6 | 6.8 | 8.1 |

Proton NMR (ppm), solvent: $D_2O$
$\delta 3.25$ (s,9H), 3.30–4.11 (m,12H), 5.43 (q,1H)
Other analyses:
Chlorine anion (wt %): 0.04
Total chlorine (wt %): 0.06
Water content (wt %): 1.12

EXAMPLE 3

Alpha-D-glucopyranose,6-(2-hydroxy-3-N,N,N-trimethylammonium propylphosphate:

One hundred parts by weight of alpha-D-glucose-6-phosphate disodium salt (trihydrate) was placed in a reactor and dissolved in 69.8 parts by weight of an aqueous 4N hydrochloric acid solution and 72.9 parts by weight of water, followed by heating to 60° C. While keeping the reaction system at 60° C., a solution of 126 parts by weight of glycidyltrimethylammonium chloride in 184 parts by weight of water was gradually dropped into the reaction system, followed by reaction at 60° C. for 5 hours. After completion of the reaction, the reaction product was purified in the same manner as in Example 1, thereby obtaining 87 parts by weight of the intended compound.

| Elemental Analysis (wt %): | C | N | H | P |
|---|---|---|---|---|
| calculated for $C_{12}H_{26}O_{10}NP$ | 38.4 | 3.7 | 6.9 | 8.3 |
| found | 38.1 | 3.8 | 6.7 | 8.5 |

Proton NMR (ppm), solvent: $D_2O$ $\delta 3.20$ (s,9H), 3.25–4.25 (m,12H), 5.25 (d,1H)
Other analyses:
Chlorine anion (wt %): 0.05
Total chlorine (wt %): 0.07
Water content (wt %): 0.93

EXAMPLE 4

Alpha-D-mannopyranose,1-(2-hydroxy-3-N,N,N-trimethylammonium propylphosphate:

One hundred parts by weight of alpha-D-mannose-1-phosphate disodium salt was placed in a reactor and dissolved in 82.2 parts by weight of an aqueous 4N hydrochloric acid solution and 85.8 parts by weight of water, followed by heating to 60° C. While keeping the reaction system at 60° C., a solution of 148 parts by weight of glycidyltrimethylammonium chloride in 217 parts by weight of water was gradually dropped into the reaction system, followed by reaction at 60° C. for 5 hours. After completion of the reaction, the reaction product was purified in the same manner as in Example 1, thereby obtaining 98 parts by weight of the intended compound.

| Elemental Analysis (wt %): | C | N | H | P |
|---|---|---|---|---|
| calculated for $C_{12}H_{26}O_{10}NP$ | 38.4 | 3.7 | 6.9 | 8.3 |
| found | 37.9 | 3.5 | 6.6 | 8.0 |

Proton NMR (ppm), solvent: $D_2O$
$\delta 3.18$ (s,9H), 3.25–4.15 (m,12H), 5.38 (q,1H)
Other analyses:
Chlorine anion (wt %): 0.11
Total chlorine (wt %): 0.13
Water content (wt %): 1.43

EXAMPLE 5

Alpha-D-galactopyranose,6-(2-hydroxy-3-N,N,N-trimethylammonium propylphosphate:

One hundred parts by weight of alpha-D-galactose-6-phosphate disodium salt was placed in a reactor and dissolved in 82.2 parts by weight of an aqueous 4N hydrochloric acid solution and 85.8 parts by weight of water, followed by heating to 60° C. While keeping the reaction system at 60° C., a solution of 148 parts by weight of glycidyltrimethylammonium chloride in 217 parts by weight of water was gradually dropped into the reaction system, followed by reaction at 60° C. for 5 hours. After completion of the reaction, the reaction product was purified in the same manner as in Example 1, thereby obtaining 101 parts by weight of the intended compound.

| Elemental Analysis (wt %): | C | N | H | P |
|---|---|---|---|---|
| calculated for $C_{12}H_{26}O_{10}NP$ | 38.4 | 3.7 | 6.9 | 8.3 |
| found | 37.9 | 3.5 | 6.6 | 8.0 |

Proton NMR (ppm), solvent: $D_2O$
$\delta$ 3.18 (s,9H), 3.25-4.29 (m,12H), 5.20 (d,1H)
Other analyses:
Chlorine anion (wt %): 0.08
Total chlorine (wt %): 1.10
Water content (wt %): 1.73

TEST EXAMPLE

The compound obtained in Example 1 and known humectants including glycerine, propylene glycol, sorbitol and urea were compared with regard to moisture absorption and moisture retention.

Moisture absorption test: 1 g of each sample was taken in a glass container and was allowed to stand under conditions of 20° C. and 98% R.H. (using a solution of $Na_2SO_4.2H_2O$), and a moisture absorption was evaluated from a change of weight with time by day.

Moisture retention test: 10 wt % of water was added to each sample and 1 g of the mixture was taken in a glass container and was allowed for 3 days under different humidity conditions of 0% R.H. (silica gel), 20% R.H. ($CH_3COOK$ solution), 44% R.H. ($K_2CO_3.2H_2O$ solution), 65% R.H. ($Mg(CH_3COO)_2.4H_2O$ solution), and 80% R.H. ($NH_4Cl$ solution). The moisture retention was evaluated from the change in weight of the sample under different humidity conditions.

The results are shown in Tables 1 and 2 below.

TABLE 1

| Moisture Absorption Test [Water Absorption (%)] | | | | | |
|---|---|---|---|---|---|
| | Days | | | | |
| Sample | 0 | 1 | 2 | 3 | 7 |
| Compound of Example 1 | 0 | 20 | 32 | 47 | 72 |
| Glycerine | 0 | 25 | 48 | 56 | 92 |
| Propylene glycol | 0 | 4 | 7 | 8 | 12 |
| Sorbitol | 0 | 7 | 12 | 20 | 30 |
| Urea | 0 | 18 | 26 | 29 | 41 |

TABLE 2

| Moisture Retention Test | | | | | |
|---|---|---|---|---|---|
| | Humidity (%) | | | | |
| Sample | 0 | 20 | 44 | 65 | 80 |
| Compound of Example 1 | −11 | −8 | 9 | 24 | 29 |
| Glycerine | −35 | −11 | 11 | 35 | 42 |
| Propylene glycol | −50 | −31 | −27 | −23 | −21 |
| Sorbitol | −50 | −28 | −22 | −18 | −13 |
| Urea | −28 | −14 | −5 | 1 | 5 |

What is claimed is:

1. A sugar phosphate of the formula (I)

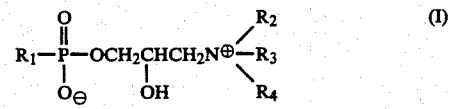

in which $R_1$ represents an active hydrogen residue of a hexose, and $R_2$, $R_3$ and $R_4$ are the same or different and represent a saturated hydrocarbon group having 1 to 4 carbon atoms or an unsaturated hydrocarbon group having from 2 to 4 carbon atoms.

2. The sugar phosphate of claim 1, wherein the said hexose is allose, altrose, galactose, glucose, gulose, idose, mannose, talose, or fructose.

3. The sugar phosphate of claim 1, wherein the hydroxyl groups of the said hexose are protected with protective groups.

4. The sugar phosphate of claim 3, wherein the said protective groups are, independently, acetyl, benzyl, benzoyl, methyleneacetal, ethylideneacetal, benzylideneacetal, or isopropylideneacetal.

5. The sugar phosphate of claim 1, wherein the said saturated hydrocarbon group is methyl, ethyl, propyl, or butyl.

6. The sugar phosphate of claim 1, wherein the said unsaturated hydrocarbon group is ethenyl, propenyl, butenyl, butadienyl, ethynyl, propynyl, butynyl, or butadiynyl.

7. The sugar phosphate of claim 1, wherein the said sugar phosphate is α-D-glucopyranose,1-(2-hydroxy-3-N,N,N-trimethylammonium propylphosphate.

8. The sugar phosphate of claim 1, wherein the said sugar phosphate is α-D-glucopyranose,1-(2-hydroxy-3N, N,N-trimethylammonium propylphosphate.

9. The sugar phosphate of claim 1, wherein the said sugar phosphate is α-D-mannopyranose,1-(2-hydroxy-3-N,N,N-trimethylammonium propylphosphate.

10. The sugar phosphate of claim 1, wherein the said sugar phosphate is α-D-galactopyranose,6-(2-hydroxy-3-N,N,N-trimethylammonium propylphosphate.

* * * * *